(12) United States Patent
Shanks et al.

(10) Patent No.: US 7,572,584 B2
(45) Date of Patent: Aug. 11, 2009

(54) SPECIES-SPECIFIC PRIMER SETS AND IDENTIFICATION OF SPECIES-SPECIFIC DNA SEQUENCES USING GENOME FRAGMENT ENRICHMENT

(75) Inventors: Orin C. Shanks, Cincinnati, OH (US); Jorge Santo Domingo, Cincinnati, OH (US); James E. Graham, Louisville, KY (US); Jingrang Lu, Mason, OH (US)

(73) Assignee: The United States of America as represented by the U.S. Environmental Protection Agency, Washington, DC (US)

( * ) Notice: Subject to any disclaimer, the term of this patent is extended or adjusted under 35 U.S.C. 154(b) by 142 days.

(21) Appl. No.: 11/316,888

(22) Filed: Dec. 27, 2005

(65) Prior Publication Data
US 2006/0275785 A1 Dec. 7, 2006

Related U.S. Application Data

(60) Provisional application No. 60/686,407, filed on Jun. 2, 2005.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3
(58) Field of Classification Search .......... 435/6; 536/23.1, 24.3
See application file for complete search history.

(56) References Cited

U.S. PATENT DOCUMENTS

| 5,436,142 | A | * | 7/1995 | Wigler et al. | 435/91.2 |
| 6,287,825 | B1 | * | 9/2001 | Weissman et al. | 435/91.2 |
| 6,316,192 | B1 | * | 11/2001 | Luo | 435/6 |
| 6,936,442 | B2 | | 8/2005 | Pichuantes et al. | |
| 2003/0228599 | A1 | * | 12/2003 | Straus | 435/6 |
| 2005/0181355 | A1 | | 8/2005 | Greener et al. | |

OTHER PUBLICATIONS

Bernhard et al. A PCR assay to discriminate human and ruminant feces on the basis of host differences in Bacteroides-Prevotella genes encoding 16S rRNA. Applied and Environmental Microbiology 66 (10) : 4571-4574 (2000).*
Diatchenko et al. Suppression subtractive hybridization: a method for generating differentially regulated or tissue-specific cDNA probes and libraries. PNAS 93 : 6025-6030 (1996).*
Galbraith et al. Suppressive subtractive hybridization as a tool for identifying genetic diversity in an environmental metagenome : the rumen as a model. Environmental microbiology 6 (9) :928-937 (2004).*
Kandpal et al. Chromosome Fishing : An affinity capture method for selective enrichment of large genomic fragments. Methods in Enzymology 216 :39-54 (1992).*
Lisitsyn et al. Cloning the differtence between two complex genomes. Science 259 :948-951 (1993).*
Makrigiorgos et al. A PCR-based amplification method retaining the quantitative difference between two complex genomes. Nature Biotechnology 20 : 936-939 (2002).*
Nguyen et al. Suppresive Subtractive hybridization of and differences in gene expression content of calcifying and noncalcifying cultures of Emiliania huxleyi strain 1516. Applied and Environmental Microbiology 71 (5) : 2564-2575 (2005).*
Straus et al. Genomic subtraction for cloning DNA corresponding to deletion mutations PNAS 87 : 1889-1893 (1990).*
Tinsley et al. Analysis of the genetic differences between *Neisseria meningitidis* and *Neisseria gonorrhoeae* : Two closely related bacteria expressing two different pathogenicities. *PNAS* 93 : 11109-11114 (1996).*

* cited by examiner

*Primary Examiner*—Ethan Whisenant
(74) *Attorney, Agent, or Firm*—Browdy & Neimark, PLLC; Anne Kornbau

(57) ABSTRACT

Targeted sequencing of genetic regions that differ between two DNA preparations uses genomic fragment enrichment. This method can be used to study genetic variation among closely related species and microbial communities.

10 Claims, 4 Drawing Sheets

Figure 4
A.  1 2 3 4 5 6 7 8 9 10 11 12
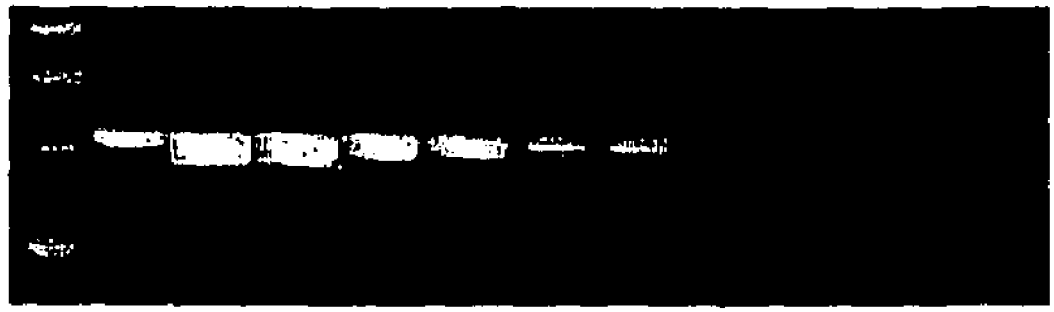
B.  1 2 3 4 5 6 7 8 9 10 11 12
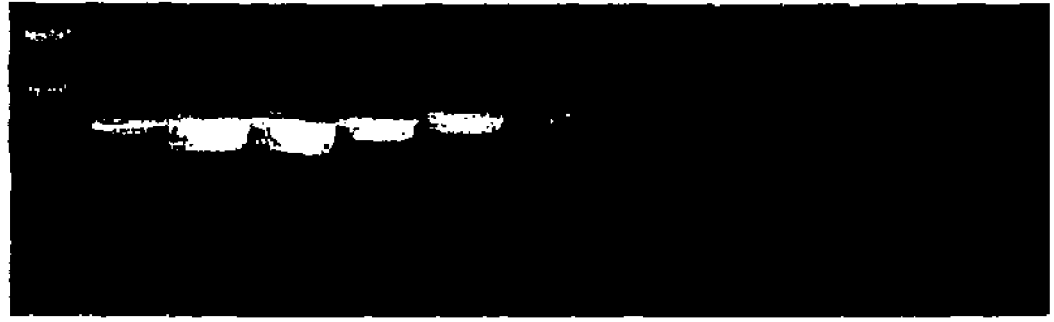
C.  1 2 3 4 5 6 7 8 9 10 11 12
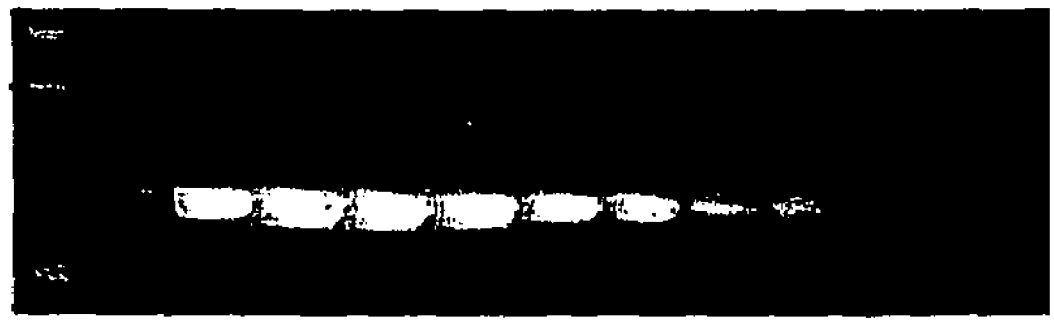

SEQUENCE LISTING

```
<160> NUMBER OF SEQ ID NOS: 39

<210> SEQ ID NO 1
<211> LENGTH: 20
<212> TYPE: DNA
<213> ORGANISM: Bacterial

<400> SEQUENCE: 1
tgcaatgtat cagcctcttc                                              20

<210> SEQ ID NO 2
<211> LENGTH: 18
<212> TYPE: DNA
<213> ORGANISM: Bacterial

<400> SEQUENCE: 2
agggcaaact cacgacag                                                18

<210> SEQ ID NO 3
<211> LENGTH: 23
<212> TYPE: DNA
<213> ORGANISM: Bacterial

<400> SEQUENCE: 3
acaagccagg tgatacagaa aga                                          23

<210> SEQ ID NO 4
<211> LENGTH: 24
<212> TYPE: DNA
<213> ORGANISM: Bacterial

<400> SEQUENCE: 4
gcttgttgcg ttccttgaga taat                                         24

<210> SEQ ID NO 5
<211> LENGTH: 23
<212> TYPE: DNA
<213> ORGANISM: Bacterial

<400> SEQUENCE: 5
ctaatggaaa atggatggta tct                                          23

<210> SEQ ID NO 6
<211> LENGTH: 18
<212> TYPE: DNA
<213> ORGANISM: Bacterial
```

-continued

<400> SEQUENCE: 6
gccgcccagc tcaaatag                                                          18

<210> SEQ ID NO 7
<211> LENGTH: 20
<212> TYPE: DNA
<213> ORGANISM: Bacterial

<400> SEQUENCE: 7
tgggaatggc ggtaatctcg                                                        20

<210> SEQ ID NO 8
<211> LENGTH: 20
<212> TYPE: DNA
<213> ORGANISM: Bacterial

<400> SEQUENCE: 8
caacagccgg tcgtcttcct                                                        20

<210> SEQ ID NO 9
<211> LENGTH: 21
<212> TYPE: DNA
<213> ORGANISM: Bacterial

<400> SEQUENCE: 9
actccctgcg ctccgaagat a                                                      21

<210> SEQ ID NO 10
<211> LENGTH: 21
<212> TYPE: DNA
<213> ORGANISM: Bacterial

<400> SEQUENCE: 10
ggcccaggca ccatttacag t                                                      21

<210> SEQ ID NO 11
<211> LENGTH: 24
<212> TYPE: DNA
<213> ORGANISM: Bacterial

<400> SEQUENCE: 11 ctccgtctttt ctccgtcctg ttct                                                  24

<210> SEQ ID NO 12
<211> LENGTH: 21
<212> TYPE: DNA
<213> ORGANISM: Bacterial

<400> SEQUENCE: 12 gatcccccctc gcctccgtcc t                                                     21

<210> SEQ ID NO 13
<211> LENGTH: 21
<212> TYPE: DNA
<213> ORGANISM: Bacterial

<400> SEQUENCE: 13
taaaggtccc ggagaaggta t                                                      21

<210> SEQ ID NO 14
<211> LENGTH: 20
<212> TYPE: DNA

<213> ORGANISM: Bacterial

<400> SEQUENCE: 14
aatccggatg cgttttttaga                                              20

<210> SEQ ID NO 15
<211> LENGTH: 22
<212> TYPE: DNA
<213> ORGANISM: Bacterial

<400> SEQUENCE: 15
cgtcaggttt gtttcggtat tg                                            22

<210> SEQ ID NO 16
<211> LENGTH: 24
<212> TYPE: DNA
<213> ORGANISM: Bacterial

<400> SEQUENCE: 16
aaggtgaagg tctggctgat gtaa                                          24

<210> SEQ ID NO 17
<211> LENGTH: 23
<212> TYPE: DNA
<213> ORGANISM: Bacterial

<400> SEQUENCE: 17
gtaattcgcg ttcttcctca cat                                           23

<210> SEQ ID NO 18
<211> LENGTH: 23
<212> TYPE: DNA
<213> ORGANISM: Bacterial

<400> SEQUENCE: 18
acctgcaaac cgtacaagaa aaa                                           23

<210> SEQ ID NO 19
<211> LENGTH: 20
<212> TYPE: DNA
<213> ORGANISM: Bacterial

<400> SEQUENCE: 19
ccaacggcgt aacttcttca                                               20

<210> SEQ ID NO 20
<211> LENGTH: 23
<212> TYPE: DNA
<213> ORGANISM: Bacterial

<400> SEQUENCE: 20
attaccggat tacaaacctt atg                                           23

<210> SEQ ID NO 21
<211> LENGTH: 20
<212> TYPE: DNA
<213> ORGANISM: Bacterial

<400> SEQUENCE: 21
tatttctggg tgcggttgta                                               20

<210> SEQ ID NO 22
<211> LENGTH: 19

```
<212> TYPE: DNA
<213> ORGANISM: Bacterial

<400> SEQUENCE: 22
ctgaccggaa tgactccca                                                   19

<210> SEQ ID NO 23
<211> LENGTH: 21
<212> TYPE: DNA
<213> ORGANISM: Bacterial

<400> SEQUENCE: 23
ctggagatca tcgttgacag a                                                21

<210> SEQ ID NO 24
<211> LENGTH: 20
<212> TYPE: DNA
<213> ORGANISM: Bacterial

<400> SEQUENCE: 24
taggctcaag cagtaccgga                                                  20

<210> SEQ ID NO 25
<211> LENGTH: 18
<212> TYPE: DNA
<213> ORGANISM: Bacterial

<400> SEQUENCE: 25
cgtgaatttc cgctacga                                                    18

<210> SEQ ID NO 26
<211> LENGTH: 18
<212> TYPE: DNA
<213> ORGANISM: Bacterial

<400> SEQUENCE: 26
cctcttcctt gcgtccca                                                    18

<210> SEQ ID NO 27
<211> LENGTH: 21
<212> TYPE: DNA
<213> ORGANISM: Bacterial

<400> SEQUENCE: 27
cggccaaata ctcctgatcg t                                                21

<210> SEQ ID NO 28
<211> LENGTH: 24
<212> TYPE: DNA
<213> ORGANISM: Bacterial

<400> SEQUENCE: 28
gcttgttgcg ttccttgaga taat                                             24

<210> SEQ ID NO 29
<211> LENGTH: 26
<212> TYPE: DNA
<213> ORGANISM: Bacterial

<400> SEQUENCE: 29
cctctaatgg aaaatggatg gtatct                                           26

<210> SEQ ID NO 30
```

```
<211> LENGTH: 24
<212> TYPE: DNA
<213> ORGANISM: Bacterial

<400> SEQUENCE: 30
ccatacttcg cctgctaata cctt                                              24

<210> SEQ ID NO 31
<211> LENGTH: 36
<212> TYPE: DNA
<213> ORGANISM: Bacterial
<220> FEATURE:
<221> NAME/KEY: misc_feature
<222> LOCATION: (1)..(1)
<223> OTHER INFORMATION: Nucleotide 1 is modified by [DFAM].
<220> FEATURE:
<221> NAME/KEY: misc_feature
<222> LOCATION: (36)..(36)
<223> OTHER INFORMATION: Nucleotide 36 is modified by [DTAM].

<400> SEQUENCE: 31
aggcacctat gtcctttacc tcatcaacta cagaca                                 36

<210> SEQ ID NO 32
<211> LENGTH: 22
<212> TYPE: DNA
<213> ORGANISM: Bacterial
<220> FEATURE:
<221> NAME/KEY: misc_feature
<222> LOCATION: (1)..(1)
<223> OTHER INFORMATION: Nucleotide 1 is modified by [DFAM].
<220> FEATURE:
<221> NAME/KEY: misc_feature
<222> LOCATION: (22)..(22)
<223> OTHER INFORMATION: Nucleotide 22 is modified by [DTAM].

<400> SEQUENCE: 32
ttatgcattg agcatcgagg cc                                                22

<210> SEQ ID NO 33
<211> LENGTH: 35
<212> TYPE: DNA
<213> ORGANISM: Bacterial
<220> FEATURE:
<221> NAME/KEY: misc_feature
<222> LOCATION: (27)..(35)
<223> OTHER INFORMATION: n is a, c, g, or t

<400> SEQUENCE: 33
gacactctcg agacatcacc ggtaccnnnn nnnnn                                  35

<210> SEQ ID NO 34
<211> LENGTH: 22
<212> TYPE: DNA
<213> ORGANISM: Bacterial

<400> SEQUENCE: 34
gacactctcg agacatcacc gg                                                22

<210> SEQ ID NO 35
<211> LENGTH: 23
<212> TYPE: DNA
<213> ORGANISM: Bacterial

<400> SEQUENCE: 35
gacactctcc gagacatcac cgg                                               23
```

```
<210> SEQ ID NO 36
<211> LENGTH: 16
<212> TYPE: DNA
<213> ORGANISM: Bacterial

<400> SEQUENCE: 36
gtaaaacgac ggccag                                                   16

<210> SEQ ID NO 37
<211> LENGTH: 17
<212> TYPE: DNA
<213> ORGANISM: Bacterial

<400> SEQUENCE: 37
caggaaacag ctatgca                                                  17

<210> SEQ ID NO 38
<211> LENGTH: 29
<212> TYPE: DNA
<213> ORGANISM: Bacterial
<220> FEATURE:
<221> NAME/KEY: misc_feature
<222> LOCATION: (21)..(29)
<223> OTHER INFORMATION: n is a, c, g, or t

<400> SEQUENCE: 38
gccggagctc tgcagaattc nnnnnnnnn                                     29

<210> SEQ ID NO 39
<211> LENGTH: 21
<212> TYPE: DNA
<213> ORGANISM: Bacterial

<400> SEQUENCE: 39
gccggagctc tgcasgaatt c                                             21
```

US 7,572,584 B2

SPECIES-SPECIFIC PRIMER SETS AND IDENTIFICATION OF SPECIES-SPECIFIC DNA SEQUENCES USING GENOME FRAGMENT ENRICHMENT

CROSS-REFERENCE TO RELATED APPLICATIONS

The present application claims priority from provisional application Ser. No. 60/686,407, filed Jun. 2, 2005, the entire contents of which are hereby incorporated by reference.

FIELD OF THE INVENTION

The present invention relates to methods for using a specific method of solution phase competitive DNA hybridization, referred to as "Genome Fragment Enrichment" to identify microbial. DNA sequences for determination of different sources of fecal contamination. The invention also relates to using this method for comparing bacterial genomes, and developing specific PCR primer sets to differentiate among bacterial species, strains, and sources of pollution.

BACKGROUND OF THE INVENTION

Current regulatory methods used to assess microbial water quality rely on measuring the levels of culturable fecal indicator bacteria such as *Enterococci* and other fecal coliforms. However, the plate culture approach cannot discriminate among different among specific bacterial strains or animal sources of fecal contamination.

There is a demand for accurate microbial source tracking (MST), because of language in the U.S. Clean Water Act regarding total maximum daily loads (TMDLs) and protection of supplies of drinking water. Current PCR-based MST approaches focus on various specific known DNA sequences, mostly targeting 16S rRNA (rDNA) genes, once thought to be source specific. However, validation studies are constantly uncovering exceptions and limitations with existing MST technologies. A significant part of the problem with existing 16S rDNA-based MST methods stemmed from the inability to target microorganism DNA sequences encoding for proteins directly involved in host-microbe interactions, which are expected to contain high levels of genetic variation related to survival within different animal hosts.

Many specific approaches have previously attempted to determine sources of fecal contamination in the environment. One of the most widely used techniques is a PCR-based method that identifies ruminant fecal pollution by targeting bacterial 16S rDNA sequences from *Bacteroides* (Bernard and Field, AEM 66:4571-4574, 2000). The present inventors have conducted ongoing validation studies of this method, and have discovered that previously described proposed ruminant specific markers can amplify rDNA from non-ruminant fecal samples collected from geographic regions outside the original watersheds sampled. By definition, these previously described PCR target regions identify cow, deer, elk, goat, sheep, and other ruminants and pseudo-ruminants. This approach is therefore less useful in watersheds impacted by more than one ruminant animal source.

While advances in DNA sequencing and computational biology allow scientists to compare entire microbial genomes and discern microorganism-specific genetic information, sequencing of multiple closely related bacterial genomes so far remains prohibitively expensive and impractical for all but a very small number of laboratories. The entire genome content of more than 238 bacterial species have so far been defined through whole genome sequencing of representative type strains, and the number of genome sequences continues to increase. While significant differences in the genome content of different species are well-established, comparisons between genomes of closely related bacteria are equally important. These comparisons can provide species and strain-specific genetic information, define metabolic pathways and virulence factors, and provide insights into capacities for host-interactions, cell-to-cell signaling, stress response, and other essential microbial cellular functions.

Current DNA-based technologies potentially capable of identifying source, species, and strain-specific genetic markers include Suppressive Subtractive Hybridization (SSH) (Diatchenko et al., *PNAS* 93:6025-6030, 1996). This technique uses intentionally biased PCR amplification of nucleic acid pools to enrich for unique segments of restricted DNA relative to non-target DNA. SSH has been successfully applied in several pair-wise comparative genome studies (e.g., Nguyen et al., 2004, *AEM* 71 2564-2575), but only on one "metagenomic" or total microbial community DNA study (Galbraith et al., 2004; *Environmental Microbiology:* 928-937). SSH is a negative selection process that relies on unequal PCR amplification to amplify all dissimilar sequences from two nucleic acid pools. This is achieved by adding different self-complementary flanking regions to each of two fragment pools, and inhibition of amplification of only those duplexes that re-anneal relative to new heteroduplexes that form following denaturation and reassociation of the mixture.

One of the limitations of currently available microbial source tracking (MST) methods arises from the inability of previously described techniques to target microorganism DNA sequences potentially encoding proteins directly involved in host-microbe interactions. These regions, unlike rDNA operons, are expected to retain high levels of genetic variation in microbes found in association with different animal hosts.

SUMMARY OF THE INVENTION

It is an object of the present invention to overcome the described deficiencies in the prior art.

It is another object of the present invention to use the Genome Fragment Enrichment (GFE) method to identify species, strain and host-specific microbial DNA sequences.

It is a further object of the present invention to provide methods for identifying whether microbial DNA from a specific animal source is present in fecal-contaminated material.

It is still another object of the present invention to identify the described DNA sequences from *Bacteroidales*-like microorganisms.

It is another object of the present invention to develop PCR primer deoxyoligonucleotide pairs to differentiate among microorganisms and host animals with respect to origins of pollution.

The present invention provides a positive DNA selection approach designated Genome Fragment Enrichment (GFE) technique, and its efficient use in identifying both unique and divergent sequences in closely related microbial genomes. Two *Enterococci* species were initially studied, *Enterococcus faecalis* (ATCC# 19433) and *Enterococcus faecium*, (ATCC# 19434). This technique can be used for many other species of microorganisms and types of environmental samples.

*Enterococci* are natural inhabitants of many animal gastrointestinal tracts, and are commonly found in sewage and animal waste. *Enterococci* are therefore frequently used as indicators of fecal pollution in environmental waters, and for human exposure risk assessments. These bacteria are also opportunistic pathogens, and cause nosocomial infections. The complete annotated genome of E. faecalis V. 583 and a draft genome assembly of E. faecium (Joint Genome Institute) are now available, allowing for an accurate post-assay assessment of the reported initial application of the Genome Fragment Enrichment (GFE) method.

Accurate identification of fecal pollution from particular animal species and individual sources is critical to assess associated health risks and to develop management plans to protect recreational water and preserve the integrity of drinking water sources (i.e., rivers and aquifers). In the United States, animal source identification methods are being applied in the development of Total Maximum Daily Loads (TMDL) as part of the Clean Water Act requirements, and in the evaluation of best management practices.

The present inventors have discovered that it is possible to prepare a set of species-specific DNA sequences utilizing GFE with total DNA extracted from fecal samples that provide the sequence information required to develop species-specific PCR primers for identifying the origin of animal fecal pollution in natural waters. The utility of these sequences was clearly demonstrated in a reduction to practice exercise in which three sequences were randomly chosen and used to design cow-specific PCR primers for detecting the presence or absence detection methods. These sequences, and the other sequences in the set for cows, are potential targets for developing PCR primers for presence or absence detection methods, real-time quantification of fecal sources, and microarray applications for risk assessment and risk management. This technique has also been applied to identify fecal contamination from chicken and human species, and to differentiate fecal pollution from these sources relative to cattle, horse, sheep, goat, pig, whitetail deer, Canadian goose, seagull, turkey, and other animals that potentially contribute to fecal pollution in a natural water source.

The present invention accelerates the identification of DNA sequences from one microorganism relative to another. For example, we identified *Enterococcus faecalis*-specific DNA sequences by using GFE to compare *E. faecalis* and *E. faecium* genomic DNA, and enrich for *E. faecalis* genome-specific DNA fragments. The two microorganisms compared, however, can be of any species, strain, or isolate if necessary.

Experiments conducted with *Enterococci* yielded 300 probable genome-specific sequences. Genome specificity was confirmed for 225 of these DNA sequences with a comparative sequence analysis using BLAST and BLAT algorithms. *E. faecalis* genome-specific sequences ranged from genes encoding phage related proteins to putative surface-exposed proteins, and even detected short regions of variation embedded in highly conserved rrn sequences. Thus, the present invention confirms the use of comparative genomics to recognize DNA loci that can be used as indicators of fecal pollution and to identify microorganism-specific genetic markers.

The present invention makes it possible, using molecular methods, to discriminate among clinically relevant species, to study the ecology of environmentally relevant microorganism species, and to identify microorganism-specific genetic markers for stress responses, virulence, carbon utilization, and cell-to-cell communication pathways.

Isolation of previously uncharacterized sequences from a microbial fecal community was made possible with the development of a DNA sorting method called Genome Fragment Enrichment (GFE). This technique is widely applicable to developing species and strain-specific PCR primers and probes, as well as to discovering novel virulence factors, use in computational toxicology, characterization of microbial communities, development of new exposure indicators, and development of methods for environmental monitoring of microbial water quality.

Genome Fragment Enrichment (GFE) uses competitive solution hybridization to obtain DNA fragments that are present in one pool of fragments but not another (as shown in FIG. 1). Labeled (e.g. biotinylated) sheared total genomic DNA from one bacterial species is first pre-hybridized with genomic DNA fragments from a second species (blocked), prior to being self-hybridized with PCR-amplified DNA fragments from the original source that contain defined terminal sequence tags (PCR primer sites). There are many conventional methods for adding defined terminal sequence tags to DNA, and any one of these methods can be used in the present invention. The DNA hybrids obtained are then isolated by binding with the label, for example biotin label binds with streptavidin, and the desired captured genomic DNA strands are then re-amplified by PCR. Thereby, DNA sequences unique to the first pool are enriched, and can be identified by subsequent cloning into *Escherichia coli* plasmids and DNA sequencing.

To identify DNA targets for microbial source tracking (MST), a metagenomic approach was used (that is, compared DNA pools were from total fecal microbial community DNA). The technical challenge was to determine a way to simultaneously compare thousands of genomes isolated from fecal samples, and identify discriminatory DNA sequences from microorganisms that have not previously been cultured or characterized.

In an initial metagenomic application of the invention, cow-specific sequences were obtained by comparing the metagenic DNA extracts derived from cow and pig fecal samples using genome fragment enrichment (GFE). GFE uses solution phase competitive nucleic acid hybridization to achieve enrichment for target molecules, as does the second step in the previously described RNA-based method for analysis of microbial gene expression Selective Capture of Transcribed Sequences (SCOTS) (Graham et al., 1999, PNAS 96: 11554-11559). SCOTS allows for the selective capture of bacterial cDNA molecules from total cDNA prepared from infected cells or tissues in a first step, using hybridization to biotinylated, bacterial, genomic DNA. These are previously well-described nucleic acid manipulation methods that are applied differently in each analysis method. Major key changes were required to use competitive nucleic acid hybridization for the DNA analysis method invented, Genome Fragment Enrichment.

Fundamental differences between SCOTS and GFE are that GFE (the present invention) identifies regions of DNA variation, rather than differentially expressed genes (as RNAs). In addition, significant differences are present in the tagging process that adds PCR primer sites to genome fragment termini, in preparation of the capturing and blocking DNA fragment pools, and metagenomic GFE applies to a larger range of DNA fragments both in size (150 bp to 1200 bp) and sequence composition (entire genomes and metagenomes). GFE is also substantially different from the currently available SSH genome subtraction method. Unlike SSH, GFE enriches for variable DNA segments using a positive physical selection process. Target DNA segments are isolated by, for example, streptavidin binding and removed from solution, washed, and eluted in a separate reaction. All target DNA strands obtained are then amplified by complementary single-primer PCR (Grothues et al., 1993; *NAR* 21: 1321-1322). SSH attempts to enrich by an unequal or biased PCR amplification itself, relying on self-complementary terminal regions to suppress amplification of molecules common to both comparison pools. Such PCR-mediated approaches are subject to inherent variability in the PCR process itself, and are not the basis for selecting desired target molecules in GFE.

Gene Fragment Enrichment (GFE) differs from previously known techniques in a variety of ways. SCOTS is a gene expression analysis method, while GFE is intended to determine the differences between microbial genomes and total environmental DNA samples. These approaches are also based on analysis of fundamentally different types of nucleic acids. For example, SCOTS requires the use of difficult RNA extraction methods and reverse transcriptase to make cDNA. This cDNA must then be sorted into bacterial and host nucleic acids by hybridization without competitor other than bacterial rDNA containing plasmid DNA. In GFE, target DNA is first extracted, then sheared by sonication, randomly primed with a Klenow DNA polymerase I reaction, and then amplified by lone-primer-PCR (Grothues et al., 1993; *NAR* 21: 1321-1322). These are just a few of the differences in these two entirely different procedures.

SCOTS also first requires three initial rounds of selection without blocking competitor in order to obtain the microbial component of cDNA from infected cells or tissues and to normalize the representation toward unit gene copy number. The blocking component of GFE is sheared native microbial DNA, while the blocking cDNA used in the subsequent SCOTS cDNA enrichment are PCR amplicons amplified from a cDNA pool. Unlike SCOTS, GFE has no procedural step or goal to normalize sequences to unit copy number, and there is no need to separate nucleic acids from the host and microbe. SSH is an optimization of Representational Difference Analysis or RDA (Lisitsyn et al. 1993). RDA relies on the difference in amplification efficiency of DNA containing two flanking PCR primer sites (exponential amplification) relative to a single site at one end (linear amplification). By hybridization of DNA strands from two pools of DNA fragments with different linker sequences, those DNA strands from the first pool that are not able to hybridize with strands from the second pool reassociate, and form superior templates for exponential PCR amplification. Hetero-hybrids that form from the annealing of complementary strands from shared DNAs in both pools have only one flanking primer target site, and those that are unique to the second pool do not have any flanking primers sites. Differential amplification of reassociated strands unique to the target pool is then achieved by their exponential increase in a subsequent polymerase chain reaction (PCR). The first is then used to obtain amplified material unique to the first nucleic acid pool. GFE, in contrast, is a physical separation process that relies on competitive hybridization to physically separate nucleic acids prior to PCR amplification (i.e., positive selection process). SSH is a PCR mediated selective process, while GFE is a physical separation method followed by an amplification step.

Subtractive hybridization (Straus and Ausubel, 1990; PNAS 87: 1889-1893) is a different physical nucleic acid separation process, and relies on the inherently difficult goal of removing all of the common DNA strands from two nucleic acid pools by hybridization (negative selection process). DNA from one source is modified for later selective binding, and is then hybridized with material from a second source. Multiple rounds of hybridization and binding are then used to physically deplete the second pool of all complementary DNA strands. This is a different process from that used in GFE in that it is a negative hybridization and removal process. In contrast, GFE uses a positive selection approach to sample only those nucleic acids that are still able to bind complementary DNA strands in the presence of a competitor from a second source. Unlike these other approaches it does not rely on removing all of the complementary sequences in two nucleic acid pools, as does subtractive hybridization. GFE is therefore inherently less prone to obtaining "false positive" or shared sequences left behind by incomplete subtractive approaches like SSH, RDA, and subtractive hybridization.

The present invention thus provides a method for identifying differences between communities of microorganisms. This process includes the following steps:

a. obtaining labeled first genomic DNA fragments from a first community (of microorganisms) in a sample and hybridizing the first genomic DNA fragments with second genomic DNA fragments from a second community of microorganisms;

b. incubating the first and second genomic fragments with additional genomic fragments from the first community of microorganisms containing defined terminal sequence tags to form DNA hybrids;

c. capturing the resulting DNA hybrids formed with tags and PCR amplification of only the tagged fragments;

d. obtaining enriched amounts of sequences unique to the first community of microorganisms; and e. identifying the enriched sequences.

The process of the present invention can be used for any microorganisms present in a sample. The sample may originate from any animal suspected of contributing to contamination of a stream or waterway, including but not limited to cattle, fowl, pigs and humans.

The primers can be modified easily using conventional software such as PRIMER EXPRESS from ABI. To modify a primer using this software, one enters the DNA sequence and designates a primer location based on data from the conventional PCR primer. The program then designs a new primer sequence that is modified to work on a real-time platform.

Alternatively, one can modify primer sequences by hand. The key information required is the DNA sequence. It is helpful to have the conventional PCR data to designate where the 3' end of the primers should be situated.

Streptavidin is used merely as an illustration of modifying and binding partners that can be used. Any suitable chemical tagging and binding technology will work with GFE.

Figure 2:
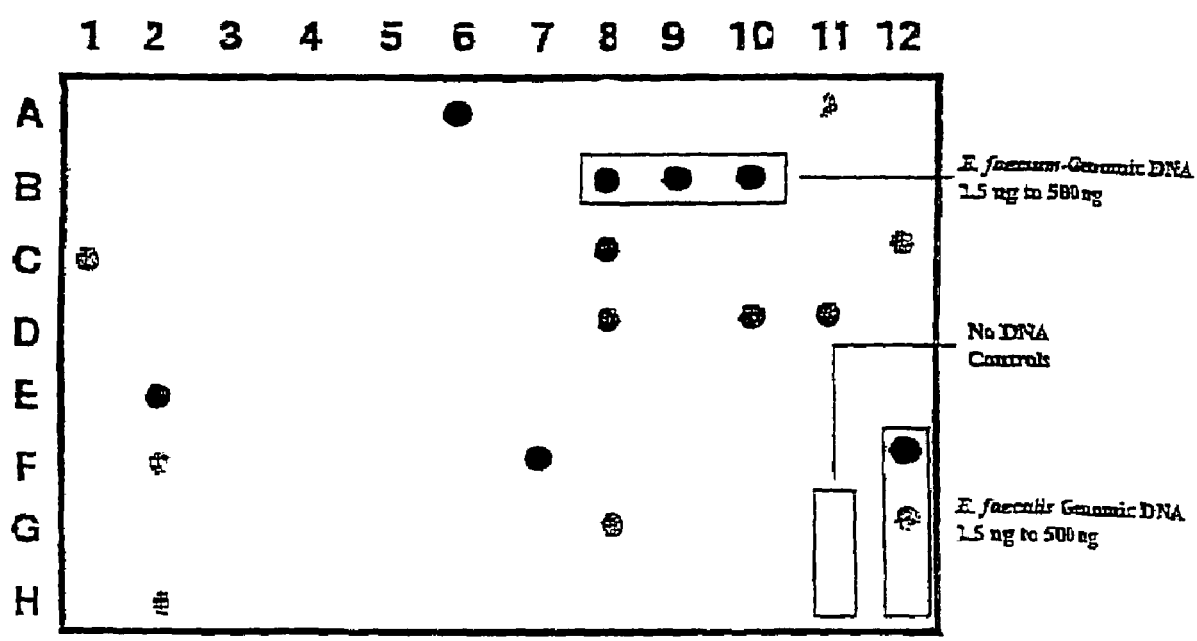

FIG. 2 shows the result of dot blot hybridization analysis of candidate *E. faecalis* (ATCC # 19433) specific DNA fragments. PCR amplicons from all non-redundant clone sequences (88 shown) were transferred to nylon membranes with a dot blot manifold and hybridized to biotin labeled *E. faecium* (ATCC# 19434) genomic DNA. Positive controls include 1.5 µ (row B, column 8), 1 µg (row B, column 9 and 500 ng) (row B, column 10), of *E. faecium* genomic DNA. The *E. faecium* genomic DNA cross-hybridized with 1.5 µg (row F, column 12), and 1 μg (row H, column 12), no DNA controls (rows G and H, column 11) did not hybridize to probe.

Figure 3:
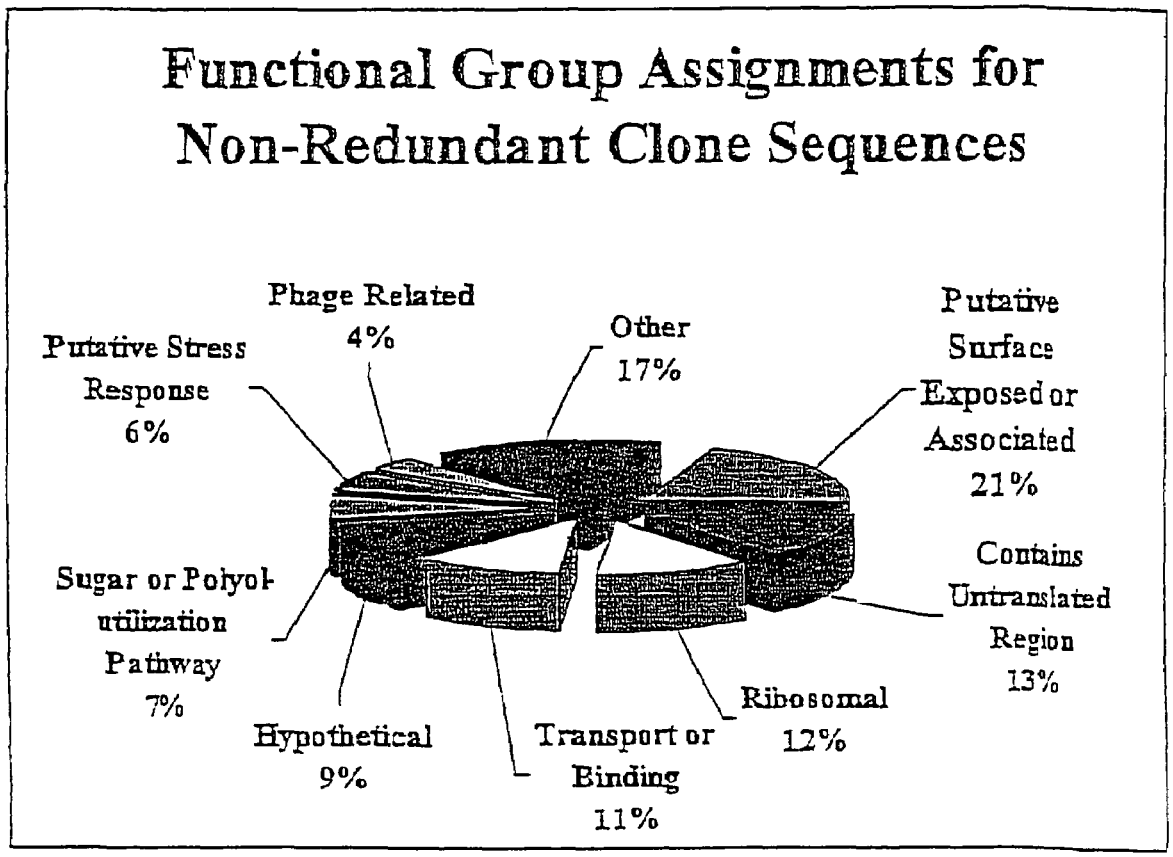

FIG. 3 shows functional group assignments for non-redundant clones.

FIGS. 4A-C illustrate the limitation of detection for host-specific primer sets using serial dilutions of cow fecal metagenomic DNA.

FIG. 4A shows that 1 fg or DNA was detected for Marker 1 (Bac1F & Bac1R).

FIG. 4B shows 10 fg of DNA was detected using Marker 2 (Bac2F & Bac2R).

FIG. 4C shows that 0.1 fg or DNA was detected with Marker 3 (Bac3F & Bac3R).

DETAILED DESCRIPTION OF THE INVENTION

Genome Fragment Enrichment

Genome fragment enrichment is useful in identifying regions of genetic variation between two microbial genomes or metagenomes of entire bacterial communities such as microbiota present in fecal material from different animal species. For microbial genome comparisons, genome fragments from one microbial species are first hybridized with genomic DNA fragments from a second microbial species, and then these fragments are incubated with additional genomic DNA fragments from the first species containing defined sequence tags. The resulting DNA hybrids are captured, and all of the captured strands from the tagged pool are PCR amplified by primers complementary to the added terminal tag sequences. These amplified DNAs are sequences unique to the first microbial species or source. Sequences obtained are then unambiguously identified by cloning into $E.$ $Coli$ plasmids and DNA sequencing.

Figure 1:
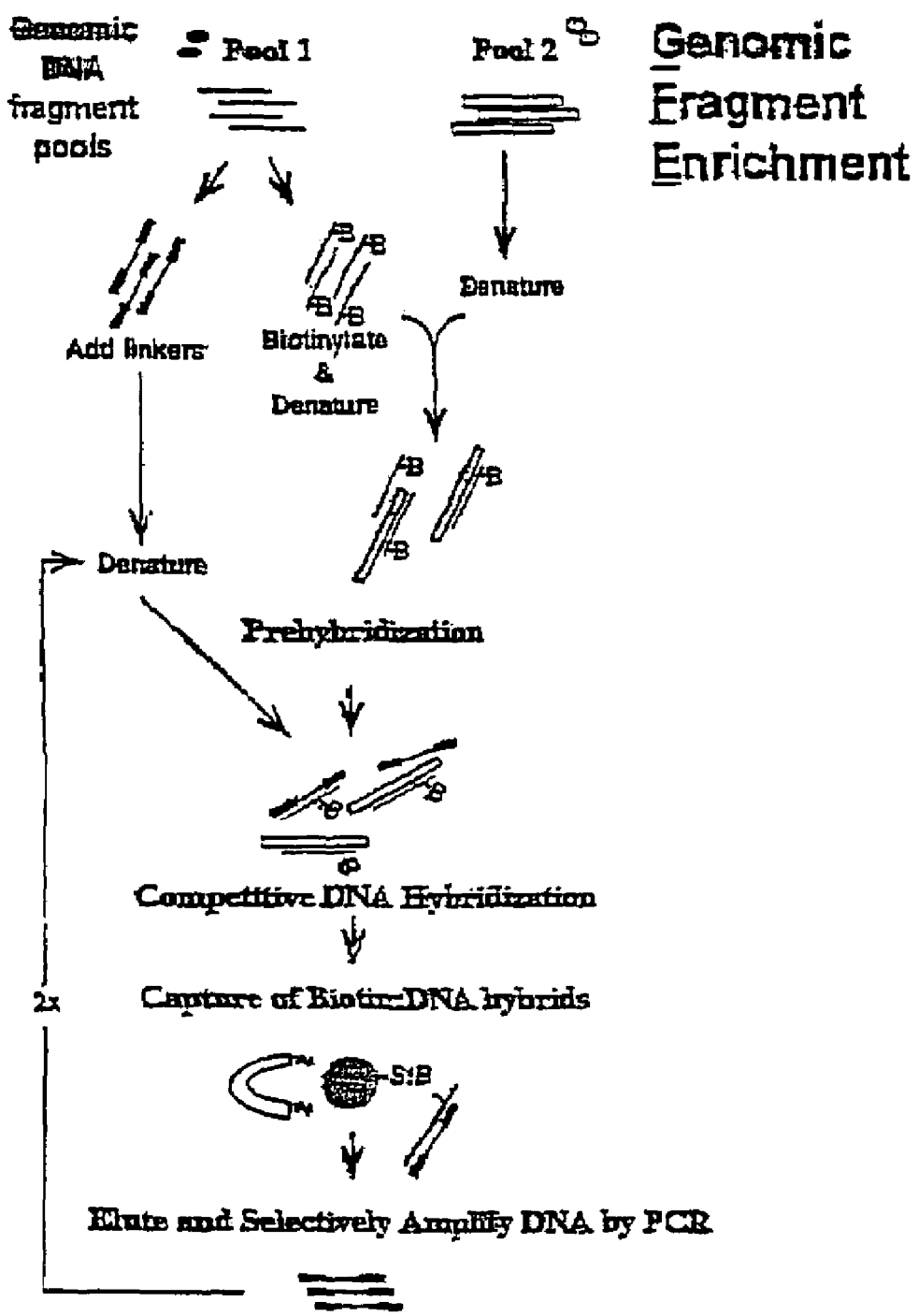
FIG. 1 illustrates a process for identifying *E. faecalis* (ATCC# 19433) DNA sequences that are absent or significantly divergent (~70%) in the *E. faecium* (ATCC# 19434) genome using GFE. Biotin-labeled genomic DNA fragments from one *E. faecalis* are first hybridized with genomic DNA fragments from *E. faecium* (blocked), prior to incubation with additional genomic DNA fragments from the original source containing defined terminal sequence tags. By capturing the resulting DNA hybrids with streptavidin and PCR amplification of only the tagged fragments, DNA sequences unique to *E. faecalis* are enriched, and can be unambiguously identified by subsequent plasmid cloning and DNA sequencing.

Genome Fragment Enrichment uses a competitive hybridization process that is also a part of the previously described RNA analysis method, SCOTS (Graham et al., 1999). As seen in the second stage of SCOTS, GFE uses competitive solution hybridization to obtain DNA fragments that are present in one pool of fragments but not in another (FIG. 1). However, unlike SCOTS, GFE targets regions of chromosomal variation, rather than differently expressed genes. Labeled sheared total genomic DNA from one bacterial species is first pre-hybridized with genomic DNA fragments from a second species (blocked), prior to being self-hybridized with PCR-amplified DNA fragments from the original source that contain defined terminal sequence tags. DNA hybrids are then isolated by, for example, streptavidin binding or any conventional chemical tagging and binding method, and the captured genomic fragments are re-amplified by PCR. Thereby, DNA sequences which are unique to the first pool are enriched and can be identified by subsequent plasmid cloning and DNA sequencing.

Genome fragment enhancement was successfully used to identify hundreds of DNA sequences which are either absent or divergent in one bacterial genome compared to another, as well as microbial cow-specific DNA sequences present in a cow fecal metagenome and absent in a pig metagenome. In addition to cow-specific DNA sequences, GFE has been successfully applied to isolate microbial human-specific and chicken-specific DNA sequences. This technique can also be used to identify DNA sequences either absent or divergent in a variety of bacterial genomes or microbial communities (i.e. fecal samples). Specific non-limiting examples of animals include cattle, human, and chicken.

Host-specific primer sets developed from DNA sequences isolated with GFE can be used for end point and real-time PCR applications, as well as microarray applications to make species-specific identifications. Conventional host-specific primer sets can readily be modified to provide real-time PCR primers. Specific non-limiting examples of animals reported herein include cattle, human, and chicken.

Laboratory Application of Genome Fragment Enrichment

Initially, 70 cow-specific DNA sequences isolated from cow fecal material were identified using the GFE method of the present invention. Three of these sequences were randomly chosen to develop cow discriminatory primer sets, and full scale working applications.

Three randomly selected host-specific Bacteroidales-like GFE sequences were used for host-specific PCR primer development (Table 1). PCR assay 1 was derived from a 368 bp host-specific DNA fragment annotated as a conserved hypothetic secretory protein with an unclassified functional group assignment (locus BT0921). The top BLASTx hit ($8.00E^{-11}$) for this sequence shared 25% sequence identity to a $B.$ $fragils$ YCH46 hypothetical protein (locus BF2432). Under optimal PCR conditions (62° C. annealing 30 cycles), PCR assay 1 routinely detected fg quantities of cow fecal DNA (FIG. 4A).

PCR assay 2 targets a portion of 437 bp fragment annotated as a HDIG domain protein involved in energy metabolism and electron transport (locus BT2749). The top BLASTx hit for PCR assay 2 (32% ID; $1.00E^{-08}$) was a $B.$ $fragils$ YCH46 putative membrane-associated HD superfamily hydrolase. Optimal conditions for PCR assay 2 include a 62° C. annealing temperature for 35 cycles, which allowed for the detection of 10 fg cow fecal DNA, as showing FIG. 4B.

PCR assay 3 originated from a 569 bp fragment encoding for a sialic acid-specific 9-O-acetylesterase secretory protein homologue (locus BT0457) functioning cell envelope biosynthesis and degradation of surface polysaccharides and lipopolysaccharides. The top BLASTx hit for marker 3 (75% ID; $8.00E^{-80}$) was a sialate O-acetylesterase protein from $B.$ $fraglis$ YCH46. PCR assay 3 exhibited the lowest limit of detection under optimal conditions (60° C.; 35 cycles) and consistently amplified 0.1 fg of cow fecal DNA (FIG. 4C). In addition, three novel PCR assays and two real-time PCR tests specific for cattle fecal microbes have also been developed and are listed in Table 1.

All host-specific markers amplified template DNA molecules from the original target GFE cow fecal sample, as well as from a large number of individual cow fecal samples not used to construct host-specific GFE clone libraries. Host-specific markers were present in 72% to 91% of 148 cow fecal samples collected from five different geographical locations over a 24-month period (Table 4). PCR assay 3 showed the broadest host distribution and temporal stability by successfully amplifying 91% of all cow fecal samples.

Each primer set was tested against individual non-target DNA molecules. PCR assay 3 exhibited specificity for 99.2% of the fecal samples and only cross-reacted with two alpaca samples. Primer sets demonstrated extremely high levels of specificity in fresh and marine natural water sources. All water samples yielded no PCR product suggesting that indigenous microorganisms from these water sources do not cross-react with host-specified target DNA sequences.

Table 1 provides a summary of host-specific PCR primer sequences, amplicon lengths in base pairs, optimal annealing temperatures (°C.), optimal number of PCR thermal cycles, and limit of detection.

TABLE 1

Optimal reaction conditions, limited of detection and primer sequences of host-specific PCR assays.

| No. | Primer Set | Sequence (5' to 3') | | Amplicon Length (bp) | Optimal Annealing Temp (°C.) | Optimal Cycle No. | Limit of Detection |
|---|---|---|---|---|---|---|---|
| 1 | Bac1F | TGCAATGTATCAGCCTCTTC; | SEQ ID NO:1 | | | | |
|   | Bac1R | AGGGCAAACTCACGACAG, | SEQ ID NO:2 | 196 bp | 62° C. | 30 | 1 fg |
| 2 | Bac2F | ACAAGCCAGGTGATACAGAAAGA; | SEQ ID NO:3 | | | | |
|   | Bac2R | GCTTGTTGCGTTCCTTGAGATAAT; | SEQ ID NO:4 | 274 bp | 62° C. | 35 | 10 fg |
| 3 | Bac3F | CTAATGGAAAATGGATGGTATCT; | SEQ ID NO:5 | | | | |
|   | Bac3R | GCCGCCCAGCTCAAATAG; | SEQ ID NO:6 | 166 bp | 60° C. | 35 | 1 ag |
| 4 | Bac4F | TGGGAATGGCGGTAATCTCG; | SEQ ID NO:7 | | | | |
|   | Bac4R | CAACAGCCGGTCGTCTTCCT; | SEQ ID NO:8 | 187 bp | 65° C. | 35 | — |
| 5 | Bac6F | ACTCCCTGCGCTCCGAAGATA; | SEQ ID NO:9 | | | | |
|   | Bac6R | GGCCCAGGCACCATTTACAGT; | SEQ ID NO:10 | 150 bp | 65° C. | 35 | — |
| 6 | Bac8F | CTCCGTCTTTCTCCGTCCTGTTCT; | SEQ ID NO:11 | | | | |
|   | Bac9R | GATCCCCCTCGCCTCCGTCCT; | SEQ ID NO:12 | 430 bp | 65° C. | 35 | — |
| 7 | Hum76Fa | TAAAGGTCCCGGAGAAGGTAT; | SEQ ID NO:13 | | | | |
|   | Hum76Ra | AATCCGGATGCGTTTTTAGA; | SEQ ID NO:14 | 209 bp | 58° C. | 35 | — |
| 9 | Hum163Fa | CGTCAGGTTTGTTTCGGTATTG; | SEQ ID NO:15 | | | | |
|   | Hum163Ra | AAGGTGAAGGTCTGGCTGATGTAA; | SEQ ID NO:16 | 165 bp | 60° C. | 35 | — |
| 11 | Hum181Fb | GTAATTCGCGTTCTTCCTCACAT; | SEQ ID NO:17 | | | | |
|   | Hum181Rb | ACCTGCAAACCGTACAAGAAAAA; | SEQ ID NO:18 | 110 bp | 61° C. | 35 | — |
| 12 | Hum336Fa | CCAACGGCGTAACTTCTTCA; | SEQ ID NO:19 | | | | |
|   | Hum336Ra | ATTACCGGATTACAAACCTTATG; | SEQ ID NO:20 | 162 bp | 62° C. | 35 | — |
| 13 | CP6F | TATTTCTGGGTGCGGTTGTA; | SEQ ID NO:21 | | | | |
|   | CP6R | CTGACCGGAATGACTCCCA; | SEQ ID NO:22 | 244 bp | 64° C. | 35 | 0.4 pg |
| 14 | CP4F | CTGGAGATCATCGTTGACAGA; | SEQ ID NO:23 | | | | |
|   | CP4R | TAGGCTCAAGCAGTACCGGA; | SEQ ID NO:24 | 445 bp | 65° C. | 35 | 40 pg |
| 15 | CB6F | CGTGAATTTCCGCTACGA; | SEQ ID NO:25 | | | | |
|   | CB6R | CCTCTTCCTTGCGTCCCA; | SEQ ID NO:26 | 287 bp | 64° C. | 35 | 4 pg |
| 16 | cowM2F | CGGCCAAATACTCCTGATCGT; | SEQ ID NO:27 | | | | |
|   | cowM2R | GCTTGTTGCGTTCCTTGAGATAAT; | SEQ ID NO:28 | 92 bp | 60° C. | 40 | — |
| 17 | cowM3F | CCTCTAATGGAAAATGGATGGTATCT; | SEQ ID NO:29 | | | | |
|   | cowM3R | CCATACTTCGCCTGCTAATACCTT; | SEQ ID NO:30 | 122 bp | 60° C. | 40 | — |
| 18 | M2probe | [DFAM] AGGCACCTATGTCCTTTACCTCATCAACTACAGACA [DTAM] | SEQ ID NO:31 | | | | |
| 19 | M3probe | [DFAM] TTATGCATTGAGCATCGAGGCC [DTAM]; | SEQ ID NO:32 | | | | |

In validation studies, all three cow-specific PCR assays were found to differentiate between cows and 29 other animal species and did not amplify DNA isolated from freshwater and marine microbial communities. These assays also successfully identified cow fecal pollution from water samples collected in two watersheds situated near cow animal feeding operations. Based upon the fact that three randomly chosen sequences worked according to plan, one skilled in the art would expect that the remaining 67 sequences would work just as well. It is also reasonable to expect that human and chicken-specific DNA sequences isolated during GFE will allow for the development of additional human- and chicken-specific PCR assays.

Genome fragment enrichment has been successfully used to identify hundreds of DNA sequences either absent or divergent in one bacterial genome compared to another, as well as microbial cow-, human-, and chicken-specific DNA sequences.

GFE Technical Protocol

A. Biotin Labeled "Capture Fragment" Preparation

While the protocol described below uses microgram quantities of DNA, GFE has been successfully performed with much smaller starting quantities of DNA. The key to using much smaller quantities of DNA is to maintain specific ratios between target, blocker, and capture surface. It is crucial to use large quantities of blocker DNA relative to the capturing surface for the prehybridization step. In some of the examples in the present specification, approximately 50 times more blocker was used than capturing surface DNA, and one-tenth the amount of capturing surface DNA for target DNA. A lower limit is approximately 1:2 and 1:1 ratios of capture:target. Ideally, one creates a competitive hybridization environment in which the blocked DNA has the advantage, both in quantity of DNA and time, to hybridize to complementary DNA sequences in the capturing surface. This advantage is realized in the prehybridization step, where competitive hybridization of the capturing surface of the capturing surface, the blocking DNA, physically blocks DNA sequences shared between two DNA pools. The unblocked DNA hybridization sites remaining after prehybridization are then available to form DNA hybrids with the terminal tagged target DNA, which is at a disadvantage to the blocker DNA both in quantity of DNA and time to hybridize.

For the comparison of two microbial genomes, *E. faecalis* genomic DNA 1.8 µg was mechanically sheared by sonication into approximately 150 to 900 base pair (bp) fragments, precipitated in 7.5 M ammonium acetate and 100% ethanol, and dissolved in 15 µg TE (1.0 mM Tris, 0.1 mM EDTA, pH 7.5). DNA was mixed with 1.8 µg of photoactive biotin (PBA; Sigma) and transferred to three 0.2 ml thin wall PCR microtubes in equal volumes to increase the surface area of direct exposure to the light source. Each microtube was placed on ice under a regular 200-watt incandescent light bulb, distance 5 cm, for 20 minutes. The three aliquots were then combined, diluted tenfold with TE (pH 9.0), and extracted with three volumes of n-butanol to remove unincorporated PAB. The supernatant was then discarded, and the remaining solution was split into three equal volumes and concentrated by ammonium acetate and ethanol precipitation.

B. Blocking DNA Preparation

Blocking DNA can be prepared in any number of ways familiar to one skilled in the art. In the present example, sheared native DNA was used rather than PCR amplified DNA in order to reduce amplification bias in the blocker DNA fragment pool.

To prepare blocking DNA for pre-hybridizing capture fragments as shown in FIG. 1, 30 µg of *E. faecium* genomic DNA were sheared, divided into three equal volumes, precipitated with 7.5 M ammonium acetate and 100% ethanol, and dissolved in 30 µl TE (10 mM Tris, 0.1 mM EDTA, pH 7.5)

C. Target DNA Preparation

Four micrograms of *E faecalis* genomic DNA were sheared by sonication, precipitated in 7.5 M ammonium acetate and 100% ethanol, and dissolved in 5 µl TE (pH 7.5). Defined terminal sequences were added to these capture target fragments to allow PCR amplification of sequences enriched by competitive hybridization. DNA fragments were re-suspended and incubated at 95° C. for five minutes with 4.5 µg K9-DNA primer (5'GACACTCTCGAGACATCACCGG-TACC-NNNNNNNNN-3'; SEQ ID NO:33). This primer illustrates one of many primers that can be used. The most important characteristics of a primer for use in the present invention are that the sequence works well for T-PCR and to have a random polymer 3'sequence. The mixture was then cooled on ice for five minutes and primers extended with 50 units DNA polymerase I Klenow fragment as described by the manufacturer (New England BioLabs) for 3.5 hours. Klenow extension products containing tagged termini were purified using a QiaQuick PCR Product Clean-up Kit (Qiagen).

A single primer amplification step was then performed to initially amplify K9-targeted DNA. This has previously been shown to produce a reasonable representation of the original material with DNA fragments of this size. Reactions (100 µl) contained 1X ExTaq PCR buffer (Invitrogen); 2.5 mM each dATP, dCTP, dGTP, and dTTP; 0.2 µM of K9-PCR primer (5'-GACACTCTCGAGACATCACCGG-3'; SEQ ID NO:34); 1% acetamide; 0.625 U ExTaq, and 10 ng of tagged DNA. Incubation temperatures were 94° C. for 40 seconds, 53° C. for one minute, and 72° C. for 30 seconds, for 28 cycles, followed by a 72° C. extension step lasting 1.5 minutes. PCR products were purified using a QiaQuick PCR Product Clean-up Kit (Qiagen).

A single primer amplification step was then performed to initially amplify K9-tagged target DNA. This has previously been shown to produce a reasonable representation of the original material with DNA fragments of this size (Tarr et al., *Journal of Bacteriology* 182: 6183-6191, 2000). Reactions of 100 µl each contained 1X ExTaq PCR buffer (Invitrogen), 2.5 mM (each) of dATP, dCTP, dGTP and dTTP, 0.2 µM of K9-PCR primer (5'-GACACTCTCCGAGACATCACCGG-3'; SEQ ID NO:35), 1% acetamide, 0.625 U Ex Taq, and 10 ng of tagged DNA. As noted above, a different primer can be used, depending upon the terminal sequence used to tag the target DNA. Incubation temperatures were 94° C. for four seconds, 53° C. for one minute, and 72° C. for 30 seconds for 28 cycles followed by a 72° C. extension step for 1.5 minutes. PCR products were purified using a QiaQuick PCR Product Clean-up Kit (Qiagen). All PCR reactions in this study were performed in either low-retention reaction tubes (0.2 ml) or 96-well polypropylene plates using a MJ Research DNA Engine Tetrad 2 thermal cycle.

The temperatures for hybridization used in GFE depend on the physical properties of the DNA used as target, blocker, and capturing surface. Hybridization temperatures from about 40° C. to about 70° C. have successfully been used in GFE.

D. Prehybridization and Capture Hybridization

Two independent full analyses were performed. For each enrichment, 10 µg of blocking *E. faecium* DNA and 0.6 µg of biotinylated *E. faecalis* capture DNA were precipitated in ethanol, resuspended in 20 µl EPPS solution (10 mM EPPS, 1 mM EDTA), overlaid with mineral oil, and incubated at 98° C. for two minutes. The incubation temperature was then reduced to 55° C., 4 µl of 5M NaCl were added immediately, and the solution was allowed to self-hybridize for 30 minutes. Five micrograms of K9-tagged *E. faecalis* PCR product was resuspended in 20 µl of EPPS solution and incubated at 98° C. for two minutes in a second microtube. These two solutions were then mixed together and incubated at 55° C.

E. Capture of Target-Specific DNA

Biotinylated DNA hybrids were isolated from the hybridization mixture with Dynabeads M-280 Streptavidin (Dynal Biotech, Brown Deer, Wis.). First, 60 µl of beads were washed with 100 µl B & W buffer (TE, pH 7.5, 2M NaCl) three times. Biotin labeled DBNA was immobilized to the bead surface by mixing washed beads and the hybridization reaction diluted in 500 µl if water at 42° C. for ten minutes. The beads were separated from the diluted hybridization mix with a magnetic particle concentrator (MPC-S; Dynal Biotech (and washed three times with 100 µl SG1 Buffer (0.5 M NaOH, 0.1 M NaCl) and incubated for ten minutes at 37° C. The resulting eluate was then precipitated in ammonium acetate and ethanol and resuspended in 80 µl TE (pH 7.5). Eluted K9-tagged target *E. faecalis* DNA molecules were selectively amplified as previously described above. The PCR products were purified, pooled, and used as target DNA for a second round of prehybridization and hybridization. The PCR products from the second round were used for a third round.

Initially, it was believed that three rounds of GFE were necessary to isolate unique DNA fragments. However, it has been found that one enrichment round is sufficient.

DNA Sequencing

PCR products from the third round of each independent GFE were incorporated into pCR4.1 TOPO as described by the manufacturer, Invitrogen. Individual clones were then subcultured in 300 µl of Luria Broth containing 10 µg/ml ampicillin, and corresponding plasmid purified prior to screening by PCR for inserts. PCR reactions (25 µl) contained 1 X ExTaq PCR buffer (Invitrogen), 2.5 mM (each) dAPT, dCTP, dGTP, and dTTP, 0.2 µM of M13F(5'-GTAAAAC-GACGGCCAG-3'; SEQ ID NO:36) and M13R (5'-CAG-GAAACAGCTATGCA-3'; SEQ ID NO:37) primers, 0.064% bovine serum albumin (Sigma), 0.625 U ExTaq and 1 µl of template. Incubation temperatures included 94° C. for three minutes lysis step followed by 20 cycle of 94° C. for 30 seconds, 52° C. for 20 seconds, and 72° C. for 40 seconds. Prior to sequencing, PCR products were purified using Qiaquick 96 Plate (Qiagen). Screening was performed in both directions at the Cincinnati Children's Hospital Medical Center Genomics Core Facility (Cincinnati, Ohio) by the dye-terminator method using an Applied Biosystems PRISM 3730 DNA Analyzer.

Dot Blot Hybridizations

To confirm genetic variation in the *E. faecalis* chromosomal regions identified, dot blot hybridizations were performed with the cloned regions using *E. faecium* DNA as a probe (Ausubel et al., 2001). PCR products for each enriched DNA sequence were purified using the QiaQuick PCR Purification Kit (Qiagen) and 10 µl of PCR product were denatured with 45 µl of denaturing solution (0.5 M NaOH, 1.5 M NaCl) prior to spotting directly onto nylon membranes (Li-cor) using a 96-2311 manifold (BioRad). The membranes were neutralized with 10 µl neutralization solution (1M TrisCl pH 8.0, 1.5 M NaCl), and UV cross-linked using a Stratalinker (Stragene) following the manufacturer's instructions. Prehybridization was performed for 1.5 hours at 65° C. in 9 ml of per-warmed Odyssey DNA Hybridization solution (Licor) containing 1X Denhardt's solution (Sigma) and salmon sperm DNA (Sigma). For probe synthesis, defined terminal sequences were added to *E. faecium* genomic DNA as described above [GFE (iii) using F9-DNA 5'-GCCG-GAGCTCTGCAGAATTC-NNNNNNNNN-3'; SEQ ID NO:38]. F9-tagged DNA was amplified as described above [GFE (iii) using biotin-16-2'deoxyuridine-5'-triphosphate (Roche) and the F9-PCR primer [5'-GCCGGAGCTCTG-CASGAATTC-3'; SEQ ID NO:39]. The F9-tagged biotin labeled *E. faecium* PCR product was purified using QiaQuick PCR Purification Kit (Qiagen). Approximately one microgram of probe (20 µl of PCR product) was added to fresh hybridization solution and allowed to hybridize spotted membranes overnight at 55° C. in a rotating hybridization oven. Standard protocols for membrane washing were followed, washing twice under low stringency conditions (room temperature) and twice under moderate stringency conditions (42° C.) (Ausubel et al., 2001). The membranes were visualized with ah Odyssey infrared imaging system (Licor) at an intensity setting of five.

Data Analysis

DNA sequence reads were assembled using SeqMan II (DNAstar, Inc.) and compared to the *E. faecalis* V583 annotated genome at The Institute for Genomic Research (TIGR) with BLASTn. Redundant sequences were removed from the data set. The remaining sequences were then searched against the *E. faecium* genome draft assembly using the JGI tBLASTx (Joint Genome Institute). The sequences were designated homologous (expectation value$\leq 1e^{-03}$) or absent (no significant hits). Gene attributes were assigned to specific clones based on annotations available at the TIGR comprehensive microbial resource database.

DNA sequence identities between *E. faecalis* (ATCC# 19433) and *E faecalis* V583 were calculated using BLASTn (Althschul et al., 1997) generated alignments. Sequence identities between *E. faecalis* (ATCC# 19433) and the *E. faecium* draft assembly (JGI) were derived from pair wise DNA sequence comparisons using the Wilbur-Lipman method with default settings (MegAlign, DNAstar, Inc.).

Non-redundant clones, false positives, and divergent clones were categorized with cross-species alignments using the JGI BLATn and the *E. faecium* genome draft assembly database. BLATn was performed with default settings and minimum sequence identity settings of 90% and 80%. Sequences were sorted into two groups using the following criteria:

A. Sequences that share a $\geq$90% sequence identity with an *E. faecium* homologue were labeled false positives, and B. sequences that did not have a match with ah 80% minimum identity were placed in the divergent clones category.

RESULTS

Summary of *E. faecalis* GFE Clones

GFE was performed with chromosomal DNA from two enterococcal ATCC type strains. Three hundred total *E. faecalis* DNA fragments between 163 and 853 base pairs in size were obtained as plasmid inserts following three rounds of GFE in two independent experiments. Analyses of these DNA fragments identified 225 non-redundant sequences (Table 2, GenBank accession numbers CZ191135-CZ191359). Several of these sequences, of 13.7% (n=31) corresponded to variable regions within ribosomal operons, including 16S, 23S and intercistronic spacer regions (ISR) DNA sequences. There are four such operons in the E. faecalis V583 genome (Paulsen et al., 2003). This large number of ribosomal clone sequences may have resulted from PCR kinetics that preferentially amplified the more abundant nucleic acid templates. These non-redundant clones from E. faecalis shared an average of 97.8% sequence with E. faecalis V583, indicating numerous strain-dependent polymorphisms, and only an average of 36% sequence identity with E. faecium (JGI) sequences, as shown in Table 2. The average identify of the enriched clone set to E. faecium was considerably lower than a set of randomly selected E. faecalis V583 genome regions, which showed an average of 58% identity to E. faecium (JGI) draft sequences. Thirty two percent (n=71) of all E. faecalis non-redundant GFE clone sequences were entirely absent from the E. faecium genome draft assembly (JGI).

GFE Sequence Characterization

As expected, BLASTn searches against the NCBI GenBank database identified homologous E. faecalis V583 sequences for all 224 non-redundant sequenced clones (Galbraith et al., 2004; Nesbo et al., 2002) (Expectation value cut-off of $\leq 1 \times 10^{-6}$) Only 154 homologous sequences in the E. faecium JGI genome draft assembly could be identified using BLASTp and tBLASTx using an expectation value cut-off of $\leq 1 \times 10^{-3}$) These E. faecalis-specific clone sequences were sorted into nine functional groups based on the annotated complete genome sequence of E. faecalis V583.

The groups consisted of the following:

1. phage open reading frames;
2. putative stress response proteins;
3. sugar or polyol utilization pathway proteins;
4. transport and binding proteins;
5. ribosomal sequences;
6. fragments containing untranslated regions;
7. hypothetical or conserved domain proteins;
8. putative surface-exposed or membrane associated proteins; and
9. others.

GFE clone groupings were based on predicted attributes. The percentages of clones conserved across all sequences low-GC Gram-positive bacteria (excluding mycoplasmas, FASTA p-value $<10^{-5}$) are listed in Table 3. The most frequently assigned gene functional group for all non-redundant GFE clones was the E. Faecalis V583 genome annotated putative surface exposed or membrane associated proteins (22.6%)(Table 3). The percentage of GFE clone sequences conserved across all known low-GC Gram-positive bacteria was only 27.2% for those sequence with an E. faecium homologue, and only 5.6% for clone sequences absent in the E. faecium genome draft assembly (Table 3).

TABLE 2

Summary of sequenced DNA clones obtained by three rounds of GFE

| E. faecalis GFE Clone Classification | No. of clones | Average Length (bp) | % Sequence ID to E. faecalis | % Sequence ID to E. faecium |
|---|---|---|---|---|
| All non-reduced clones | 225 | 401 | 97.8% | 36% |
| Homolog present in E. faecium | 154 | 410 | 98% | 64.5% |
| No homolog present in E. faecium | 71 | 380 | 96.8% | 0% |
| False positive clones | 32 | 424 | 99% | 95% |
| ($\geq$90% ID to E. faecium homolog) | 184 | 399 | 97.6% | 34.4% |
| Divergent clones ($\leq$80% ID to E. faecium homolog) | | | | |

TABLE 3

Functional group assignment of non-redundant GFE clones and percent and conserved among all sequenced low-GC Gram-positive bacteria[a]

| E. faecalis GFE Clone Classification | No. | Sur | UTR | Rib | Hyp | Tran | Path | Str | Ph | % Con |
|---|---|---|---|---|---|---|---|---|---|---|
| All non-reduced clones | 225 | 51 | 34 | 31 | 23 | 27 | 18 | 15 | 10 | 20.4% |
| Homolog present in E. faecium | 154 | 32 | 26 | 31 | 7 | 20 | 15 | 13 | 4 | 27.2% |
| No homolog present in E. faecium | 71 | 19 | 8 | 0 | 16 | 7 | 3 | 2 | 6 | 5.6% |
| False positive clones | 32 | 1 | 0 | 31 | 0 | 0 | 0 | 0 | 0 | 100% |
| ($\geq$90% ID to E. faecium homolog) Divergent clones ($\leq$80% ID to E. faecium homolog) | 184 | 50 | 31 | 0 | 23 | 26 | 17 | 13 | 10 | 22.8% |

Thirty four *E. faecalis*-specific DNA regions were identified by GFE (Table 4) using a more stringent criterion of at least two corresponding GFE clones. For example, five non-redundant GFE clones corresponded to a region predicted to encode for a 5'-nucleotidase family protein and adjacent putative pheromone binding protein (*E. faecalis* V583, segment 1; region 64,598 to 66,703). Fourteen divergent gene regions potentially encode for proteins annotated as surface exposed or membrane associated open reading frames (Paulsen et al., 2003). In the two independent GFE hybridizations, 76.5% of these 34 DNA regions were identified in both experiments (Table 4), demonstrating good consistency for the method.

Identification of False Positives and Divergent Clones

Cross-species alignments with JGI BLATn identified 32 false positive final GFE clones (≧90% identity with an *E. faecium* homologue) and 184 significantly divergent clone regions (≦80% identity with an *E. faecium* homologue). These 90% and 80% cut-offs were selected based on data from previous genome studies. rDNA clone sequences made up all of these false positives (97%) except for a cell wall surface anchor family protein (locus EFI1896, coordinates 6208-6525). The sequence identity of this cell wall surface anchor family protein was only 89%, but it remained a significant hit with the *E. faecium* JGI BLATn search because of a 40 bp stretch contained a 90% or greater DNA sequence identity.

Dot blots using *E. faecium* genomic DNA as a probe identified 62 cross-hybridizing false positive DNA sequences (FIG. 4). These clone inserts exhibited an average of a 69% sequence identity to *E. faecium* homologous sequences. Dot blot analysis correctly recognized 31 of 32 (97%) of the false positives calculated from the BLATn false positive screen, demonstrating a high level of agreement between the bioinformatics and experimental false positive screens.

Of the 71 clone sequences completely absent in *E. faecium* (table 2), only 7 elicited positive results with the dot blot assay (9.8%). These sequences may have very short regions capable of probe hybridization. These results provide experimental confirmation that numerous regions of genetic variation have been identified for these two specific ATCC strains, and are in good agreement with bioinformatic analyses based on the two sequenced strains. Over 90% of GFE sequences absent from the *E. faecium* genome draft (JGI) also showed no hybridization in the analyses conducted. Dot-blot hybridization also provides a valuable secondary screening method to identify directly GFE false positives when bioinformatic information is not available.

Identification of *E. faecalis* DNA Sequences Absent or Divergent in *E. faecium*

Several hundred candidate *E. faecalis*-specific DNA sequences were obtained by GFE, and specificity was confirmed for a subset of these genomic regions confirmed by dot blot hybridization and a comparative bioinformatic analysis. GFE clones (excluding false positives identified by BLATn) exhibited an average of only 36% DNA sequence identify with. *E. faecium* sequences (JGI), and approximately one third of these sequences were completely absent in the draft genome. Non-ribosomal GFE sequences also encoded for 34 variable *E. faecalis* chromosomal regions, of which approximately 75% were independently determined in separate experiments (Table 4).

GFE was found to be a valid approach for identifying genetic differences between closely related microbial genomes. Using this technique, the following were observed:

1. low average sequence identity for GFE sequences in the *E. faecium* genome;
2. the same variable chromosomal regions identified in two parallel experiments;
3. agreement of bioinformatic and experimental secondary screens for the specific strains studied; and
4. the absence of a high percentage of GFE clone sequences in the *E. faecium* draft genome (JGI).

While only a fraction of the clones from the enriched GFE libraries were sequenced, it is expected that additional cloning and sequencing would identify additional regions of genetic variation.

GFE Identified Regions of Variation within Highly Conserved DNA Sequences

The most highly conserved and relatively abundant sequences in the *E. faecalis* V583 genome are four ribosomal RNA (rrn) operons. Thirty one non-redundant clones were isolated, corresponding to ribosomal ISRs (n−3), 23S rRNA genes (n=22), and 16S rRNA genes (n=5). Ribosomal clones shared an average of 95.2% sequence identity with *E. faecium* homologous sequences, and were classified as false positives using the thresholds described above. However, short regions within 16S, 23S and ISR rrn sequences are also commonly used to differentiate between enterococci species (Patel et al., 1998; Monstein et al., 1998; Williams et al., 1001; Tsiodras et al., 2000; Gurtler et al., 1999; Hall, 1994; Naimi et al., 1997). For example, there are 59 polymorphic nucleotide positions (97.3% sequence identity) between two representative 16S rDNA sequences (Patel et al., 1998). There are only 14 such polymorphic nucleotides in a 300 bp stretch within domain V of the downstream 23S rDNA gene, and all 22 non-redundant 23S r DNA clones obtained by GFE fell within this variable domain V region.

ISR sequences are also widely recognized for their sequence variability and utility in both species identification and strain typing. Previous studies on *E. faecalis* report 16S-23S ISR sequence citations in the rrn operons, including the presence or absence of a tRNA$^{ala}$ gene, and a small number of intraspecies nucleotide substitutions (Gurtler et al., 1999; Hall, 1994; Neimi et al., 1997). Two GFE clones tested contained these previously described 16S-23S ISR sequences, one encoding for the tRNA$^{ala}$ gene, and one not. This indicates two distinct *E. faecalis* rrn operons in the ATCC# 19433 strain. No tRNA-containing ISR sequences appeared in the *E. faecium* draft genome (JGI), as a BLASTn of this ISR sequence was unable to identify any similar sequences. These results demonstrate that GFE was able to obtain previously described species-specific short variable regions within highly conserved DNA sequences.

Identified *E. faecalis* Genome Diversity Predominantly Represented in Surface Associated Sequences Genomic regions identified by GFE were predominantly genes predicted to encode for surface associated proteins. *E. faecium* V583 genome annotations indicating putative surface exposed or membrane associated proteins corresponded to 22.6% of the non-redundant GFE claims (Table 3). The overall frequency of genes annotated as encoding surface associated proteins in the genome is almost three times lower (6.4%). This over-representation suggests that one of the major differences between these species is the composition of proteins associated with the bacterial cell wall. Large sequence variation in genes involved in surface structures has also been observed in *Thermotoga maritime* (Nesbo et al., 2002) and also among several closely related pathogens (e.g., *Escherichia coli* 055 and 0157) genomes (Selander et al., 1997; Tarr et al., 2000; Tettelin et al., 2001; Tettelin et al., 2000). These observations are consistent with the idea that the genetic capacity for diverse surface proteins may be characteristic of the differences between closely related microorganisms. Several studies also suggest that this type of variation is due to diversifying selection pressure to avoid different host immune responses (Selander et al., 1997; Tettelin et al., 2000; Maiden et al., 1997). If this class of potential genetic markets does reflect proposed genetic variation, they would be of particular interest for the use of GFE in pathogenicity studies.

Host-Specific PCR Primers Targeting Bacteriodales-Like Sequences Exhibit a Wide Host Distribution Among Cattle In another study, GFE was used to enrich for DNA fragments isolated from an individual cow fecal metagenome that are absent in a single pig fecal metagenome. Dot blots confirmed the specificity of almost all GFE sequences for the cow fecal metagenome. In addition, three host-specific PCR primer sets were designed and optimized to target randomly selected GFE Bacteriodales-like DNA sequences (Table 1). All primer sets differentiated between the GFE target (cow) and blocker (pig) metagenomic DNA fragment pools, further demonstrating that GFE is a powerful approach for comparing two complex microbial communities. The ability of GFE to isolate DNA sequence between microbial communities was further demonstrated in similar experiments designed to select for microbial DNA sequences specific to human and chicken bacterial fecal communities.

Primers were then tested against 148 cow fecal samples to measure host distribution (Table 4). Host-specific PCR assays routinely amplified more than 80% of the cow fecal samples, regardless of geographic location. Host-specific PCR assays also showed remarkable stability within host animals over a 24-month time period. This surprising geographic and temporal stability, as well as widespread distribution among host populations, was unexpected, considering that GFE was limited to the comparison of two individual fecal samples.

Host-Specific PCR Primers Discriminate Among Many Animal Species

The unexpected stability and broad distribution of the PCR assays in cattle populations led to testing target specificity among other animal groups. All three host-specific primer sets showed extremely high levels of host specificity for cattle (Table 5), and are consistent with 16S rDNA phylogenetic studies reporting the presence of *Bacteroidales* host-specific endemic subpopulations in various animal fecal samples (Bernard and Field, 2000; Dick, 2005). Data also corroborates the notion that genes encoding for proteins directly involved in host-fecal microbe interactions will exhibit increased levels of specificity over 16S rRNA gene sequences (Simpson, 2002; Scott, 2004; Griffin, 1999; Jiang, 2001). Current 16S rDNA host-specific PCR assays can only discriminate between ruminant and non-ruminant fecal sources (Bernard and Field, 2000). Host-specific primers targeting non-ribosomal sequences differentiated between cattle and five other ruminant or pseudo-ruminant species including goat, sheep, alpaca, llama, and whitetail deer, with the exception of PCR assay 3, which cross-reacted with two alpaca fecal samples.

The present invention provides a widely applicable nucleic acid sorting method and its use in identifying regions of genetic variation between any two preparations of DNA such as two bacterial genomes or samples containing two microbial communities. GFE was able to identify *E. faecalis* DNA sequences that are absent in *E. faecium*, as well as cattle-, human-, and chicken-specific DNA sequences that are divergent or absent in other animal species fecal microbial communities. GFE provides a directed alternative to random genome sequencing for identifying genetic variation among bacterial genomes or microbial communities.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above. It is intended that such expressions be given their broadest interpretation.

REFERENCES

Althschul, S. F., Thomas, F., Madden, L., Scaffer, A., Zhang, J., Zhang, Z., Miller, W. and Lipman, D. (1997) *Nucleic Acids Research*, 25, 3389-3402.

Ausubel, F. M., Brent, R., Kingston, R. E., Moore, D. D., Seidman, J. G., Smith, J. A. and Struhl, K. (2001) *Current Protocols in Molecular Biology*, John Willey & Sons, New York.

Boucher, Y., Nesbø, C. L. and Doolittle, W. F. (2001) *Current Opinion in Microbiology*, 4, 285-289.

Dufour, A. P. (1984). U.S. Environmental Protection Agency, Cincinnati.

Galbraith, E. A., Antonopoulus, D. A. and White, B. A. (2004) *Environmental Microbiology*, 6, 928-937.

Graham, J. E. and Clark-Curtis, J. E. (1999) *Proceedings of the National Academy of Sciences of the United States of America*, 96, 11554-11559.

Grothues, D., Cantor, C. R. and Smith, C. L. (1993) *Nucleic Acids Research*, 21, 1321-1322.

Gürtler, V., YuJun, R. Pearson, S. R., Bates, S. M. and Mayall, B. C. (1999) *Microbiology*, 145, 1785-1796.

Hall, L. (1994) *Microbiology*, 140, 197-204.

Harwood, V. J., Delahoya, N. C., Ulrich, R. M., Kramer, M. F., Whitlock, J. E., Garey, J. R. and Lim, D. V. (2004) *Letters in Applied Microbiology*, 38, 476-482.

Kent, W. J. (2002) *Genome Research*, 12, 656-664.

Maiden, M. C. J., Suker, J. and Faevers, I. M. (1997) In van der Zeijst, B. A. M., Hoekstra, W. P. M., and van Embden, J. D. A. (ed.), *Ecology of pathogenic bacteria: molecular and evolutionary aspects*. Royal Netherlands Academy of Arts and Sciences, Amsterdam, pp. 15-43.

McLeod, M. P., Qin, X., Karpathy, S. E., Gioia, J., Highlander, S. K., Fox, G. E., McNeill, T. Z., Jiang, H., Muzny, D., Jacob, L. S. et al. (2004) *Science*, 186, 5842-5855.

Monstein, H. J., Quednau, H. J., Samuelsson, A., Ahrné, S., Isaksson, B. and Jonasson, J. (1998) *Microbiology*, 144, 1171-1179.

Naimi, A., Beck, G. and Branlant, C. (1997) *Microbiology*, 143, 823-834.

Nesbø, C. L., Nelson, K. E. and Doolittle, W. F. (2002) *Journal of Bacteriology*, 184, 4475-4488.

Patel, R. Piper, K. E., Rouse, M. S., Steckelberg, J. M., Uhl, J. R., Kohner, P., Hopkins, M. K., Cockerill, F. R., III and Kline, B. C. (1998) *Journal of Clinical Microbiology*, 36, 3399-3407.

Paulsen, I. T., Banerjei, L., Myers, G. S., Nelson, K. E., Seshadri, R., Read, T. D., Fouts, D. E., Eisen, J. A., Gill, S. R., Heidelberg, J. F., et al. (2003) *Science*, 299, 2071-2074.

Schaberg, D. R., Culver, D. H. and Gaynes, R. P. (1991) *American Journal of Medicine*, 91, 72S-75S.

Selander, R. K. (1997) In van der Zeijst, B. A., Hoekstra, W. P. M., and van Embden, J. D. A. (ed.), *Ecology of pathogenic bacteria: molecular and evolutionary aspects*. Royal Netherlands Academy of Arts and Sciences, Amsterdam, pp. 191-213.

Tarr, P. I., Schoening, L. M., Yea, Y. L., Ward, T. R., Jelacic, S. and Whittman, T. S. (2000) *Journal of Bacteriology*, 182, 6183-6191.

Tettelin, H., Nelson, K. E., Paulsen, I. T., Eisen, J. A., Read, T. D., Peterson, S. Heidelberg, J., DeBoy, R. T., Haft, D. H., Dodson, R. J. et al. (2001) *Science*, 293, 498-506.

Tettelin, H., Saunders, N. J., Heilderberg, J., Jeffries, A. C., Nelson, K. E., Eisen, J. A., Ketchum, K. A., Hood, D. W., Peden, J. F., Dodson, R. J. et al. (2000) *Sciences*, 287, 1809-1815.

Tsiodras, S., Golds, H. S., Coakely, E. P. G., Wennersten, C., Jr., M. and R. C. E., G. M. (2000) *Journal of Clinical Microbiology*, 38, 3991-3993.

Wilbur, W. J. and Lipman, D. J. (1983) *Proceedings of the National Academy of Sciences of the United States of America*, 80, 726-730.

Williams, A. M., Rodrigues, U. M. and Collins, M. D. (1991) *Research in Microbiology*, 145, 64-67.

---

What is claimed is:

1. A method for identifying differences between communities of microorganisms comprising:
   a) obtaining labeled first genomic DNA fragments from a first community and hybridizing the first genomic DNA fragments with second genomic DNA fragments from a second community;
   b) incubating the first and second genomic fragments with additional genomic fragments from the first community, said additional genomic fragments containing defined terminal sequence tags to form DNA hybrids;
   c) capturing the resulting DNA hybrids formed with tags and PCR amplification of only the tagged fragments;
   d) obtaining enriched amounts of sequences unique to the first community; and
   e) identifying the enriched sequences to determine between said communities.

2. The method according to claim 1 wherein the tagged fragments are modified to work in real-time PCR assays.

3. The method according to claim 1 wherein the DNA is isolated from bacterial microorganisms.

4. The method according to claim 2 wherein a first and a second microorganism are identified, wherein the first microorganism is *E. faecalis* and the second microorganism is *E. faecium*.

5. The method according to claim 1 wherein the first genomic DNA is labeled with biotin.

6. The method according to claim 1 wherein the first community is associated with cows.

7. The method according to claim 1 wherein the first community is associated with chickens.

8. The method according to claim 1 wherein the first community is associated with humans.

9. A method for identifying genetic differences between two microbial genomes comprising:
   a) obtaining labeled first genomic DNA fragments from a first microorganism and hybridizing the first genomic DNA fragments with second genomic DNA fragments from a second microorganism;
   b) incubating the first and second genomic fragments with additional genomic fragments from the first microorganism, said additional genomic fragments containing defined terminal sequence tags;
   c) capturing the resulting DNA hybrids formed with tags and PCR amplification of only the tagged fragments;
   d) obtaining enriched amounts of sequences unique to the first microorganism; and
   e) identifying the enriched sequences to determine the genetic differences between the two microbial genomes.

10. The method according to claim 9 wherein the tagged fragments are modified to work in real-time PCR.

* * * * *